United States Patent [19]
Knotts et al.

[11] Patent Number: 5,107,854
[45] Date of Patent: Apr. 28, 1992

[54] ORTHOPEDIC LIMB LOAD MONITOR

[75] Inventors: Sarah A. Knotts, Boulder; James D. Little, Longmont; Brett R. Skelton, Louisville, all of Colo.

[73] Assignee: Boulder Impact Monitors, Inc., Boulder, Colo.

[21] Appl. No.: 600,003

[22] Filed: Oct. 17, 1990

Related U.S. Application Data

[63] Continuation of Ser. No. 354,512, May 19, 1989, abandoned.

[51] Int. Cl.⁵ .............................................. A61B 5/103
[52] U.S. Cl. ..................................... 128/779; 73/172; 73/723; 340/626
[58] Field of Search ................ 128/774, 779; 33/3 A; 340/573, 626; 73/172, 715, 723-731

[56] References Cited

U.S. PATENT DOCUMENTS
4,626,244 12/1986 Reinicke ..................... 128/DIG. 12
4,899,747 2/1990 Garren et al. ..................... 606/192

FOREIGN PATENT DOCUMENTS
3631923 3/1988 Fed. Rep. of Germany ...... 128/779

Primary Examiner—Randy C. Shay
Attorney, Agent, or Firm—Rosen, Dainow & Jacobs

[57] ABSTRACT

An orthopedic exercise chamber such as a slipper including a light-weight, self-contained limb load monitor is disclosed. The limb load sensor circuit provides extended service life for the miniature power supply that is included in the slipper, thereby making the slipper suitable for out-patient use. A fluid-filled plantar chamber that supports the entire load borne by the patient's foot is connected to the sensor circuit, thereby providing improved monitoring of the load being carried by the leg or foot that must be protected from excessive loading.

18 Claims, 2 Drawing Sheets

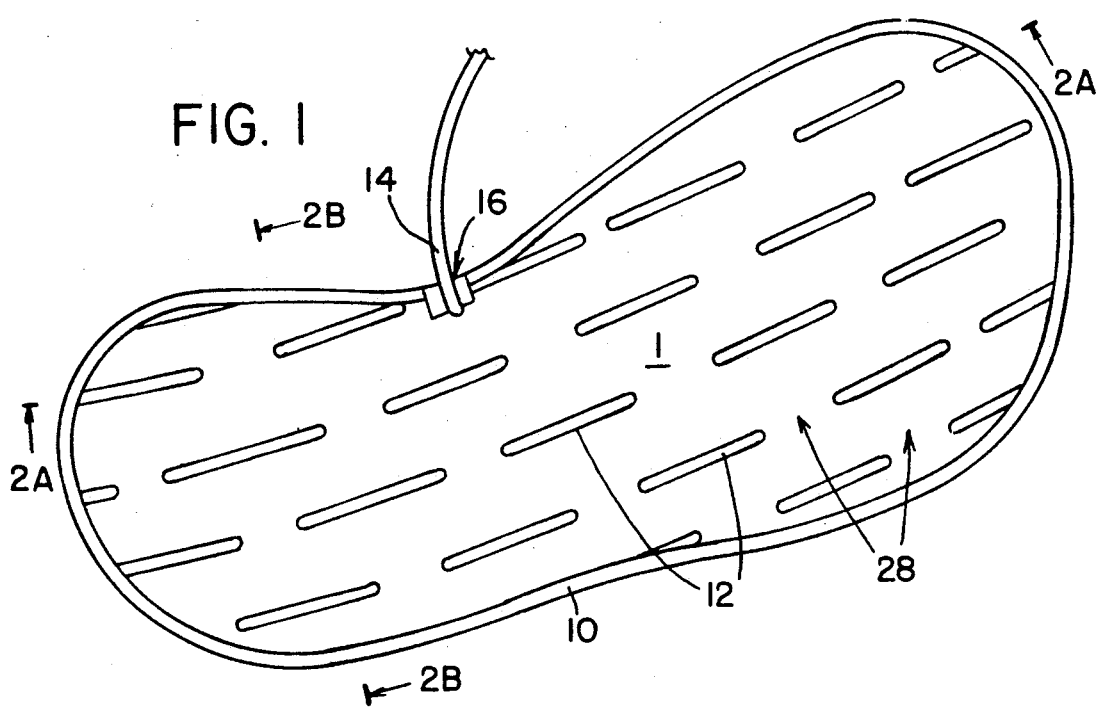
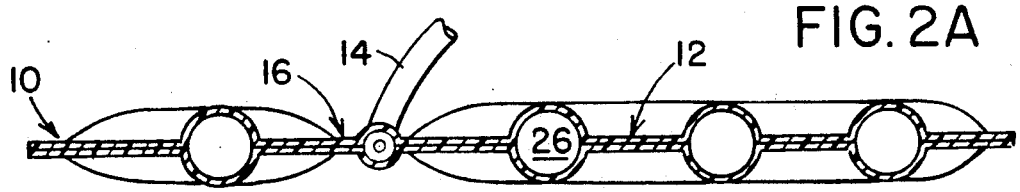
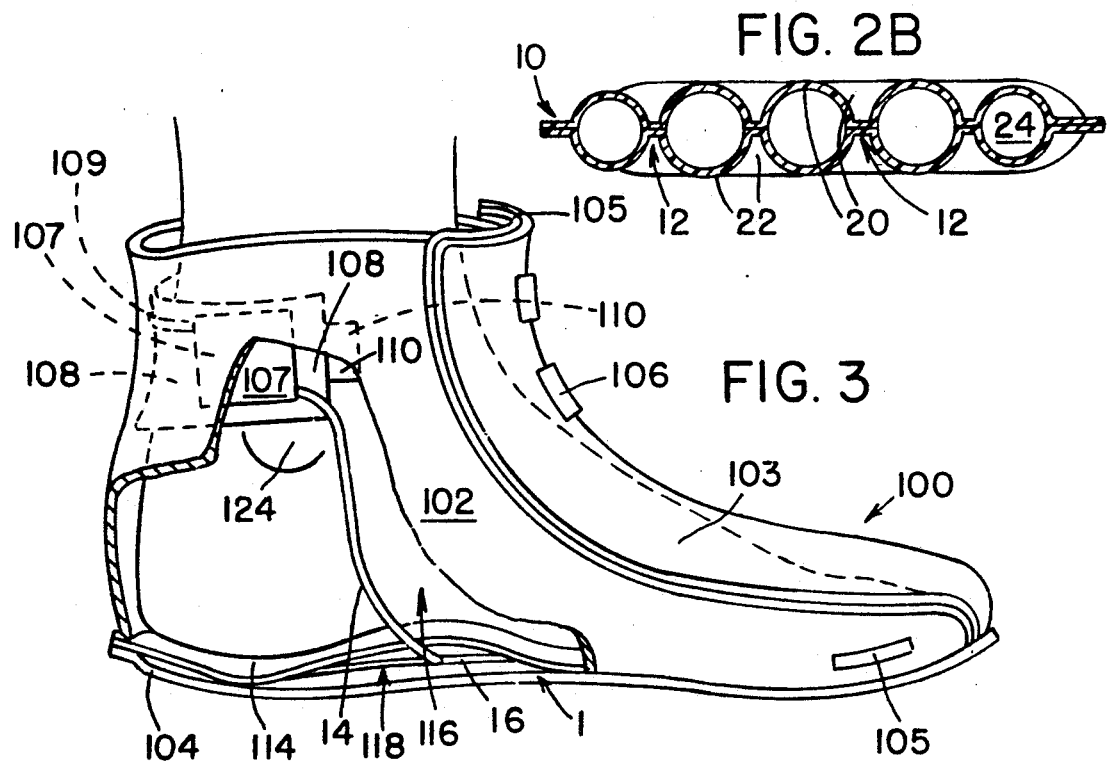

ORTHOPEDIC LIMB LOAD MONITOR

This application is a continuation in part of prior application Ser. No. 07/354,512, filed May 19, 1989, now abandoned.

BACKGROUND OF THE INVENTION

The present invention relates to orthopedic load sensors. More particularly the present invention is related to a fluid chamber for sensors that monitor the load borne by a limb to prevent harmful over-loading of the limb.

Orthopedic physical therapy programs commonly include a training period in which limited weight-bearing use of the affected limb is required for rehabilitation. The amount of weight shifted to the affected limb, however, must be carefully monitored. Of particular concern are those patients fitted with internal or external fixation devices, or joint prostheses, and those patients recovering from repair of the interior cruciate ligament in the knee. Also, research has shown that moderate, intermittent loading of a bone fracture enhances bone growth and shortens the patients' recovery time.

U.S. Pat. No. 3,791,375 discloses a fluid-filled load cell used for sensing the weight applied to a patient's limb to limit the weight borne by that limb during the patient's recovery. The load cell is made of circular, substantially rigid upper and lower plates that are maintained in a spaced relation to each other by a elastic spacer. A load cell is placed beneath the sole and beneath the heel of the patient's shoe, inside pads that approximate the outline of the sole and heel of the patient's shoe, respectively. These pads are then held in place by an ordinary rubber overshoe, which is worn over the patient's shoe.

This device, however, will produce inaccurately low readings for those patients who apply weight on the limb that is not centered over the load cells. These load cells are accurate for forces acting through them, but many patients will occasionally place their weight on one side of the affected foot or, alternatively, balance backward toward the heel or forward toward the toes of the affected foot. In such instances, these loads do not pass through the cells, but through their "spacer" elements, and may not detect the entire load acting on the limb. The resulting failure to detect excessive force can result in injury to the patient.

U.S. Pat. No. 3,974,491 discloses a sensor having a fluid-filled chamber that is a continuous, resilient tube having a circular cross section. This tube is coiled under the heel and sole of a patient's foot, inside a sponge rubber foot pad that is sandwiched between adhesive sheets of a flexible, dimensionally table material such as rubber-coated fabric.

This foot pad does not measure the total load placed on the limb, because (1) a portion of that load is borne by the sponge rubber pad rather than by the tubular sensing chamber, and (2) because the tube is not directly beneath all parts of the foot which the patient can place weight upon (e.g. the side of the foot, or the toes). Thus, this sensing chamber does not provide a reliable measure of the weight borne by the patient's limb.

German Offenlegungsschrift 3 631 923 also discloses a foot pad for measuring forces in a shoe. In this arrangement, the chamber is in the form of either an undulating tube, or a chamber having an internal spacer separating upper and lower sheets. The spacer is in the form of an intermediate layer in the chamber that has holes extending therethrough to define channels and to hold the upper and lower walls of the chamber apart. Neither of these arrangement uniformly support the foot on the pressure sensing fluid, and, when spacers are used, the spacers take up a part of the load.

These references do not consider various safety aspects of the fluid that is used in the chamber, nor do they consider the problem of reactions between the fluid and the material of the chamber.

SUMMARY

The object of the present invention is to provide a load monitor that senses the entire load borne by the patient's limb.

Another object of the present invention is to provide a limb load monitor that is accurate despite changes in the distribution and concentration of the patient's weight on the plantar surface of the patient's foot.

Another, more particular object of the present invention is to provide a self-contained monitoring foot covering such as a clipper or the like suitable for use in physical therapy exercises.

A further particular object of the present invention is to provide a monitoring foot covering or the like that can be continuously worn by the patient without discomfort or inconvenience.

A further particular object of the present invention is to provide an exercise slipper that provides for the dorsoflexion of the foot, to overcome foot-drop.

A further particular object of the present invention is to provide an exercise slipper having a fluid-filled plantar cushion to help prevent decubitis ulcers.

The present invention achieves these and other objects by providing a miniature monitoring circuit, including an extended-life power supply that is small enough and light-weight enough to be enclosed in the cuff of a slipper, and a flexible fluid plantar chamber. The flexible chamber is made up of a plurality of tubular portions that have a circular cross section and are adapted to be in fluid communication with each other. The chamber supports the entire weight borne by the patient's limb.

The chamber comprises first and second flexible sheets. The sheets are sealed together around their perimeter to form a fluid-tight chamber and affixed to the each other within that perimeter by welds. The welds between the flexible sheets are spaced so that the sheets form multiple tubular portions between the welds. No internal spacers are provided between the flexible sheets to hold the flexible sheets apart. In other words, no apertured intermediate spacing layer (as in the above discussed Offenlegungsschrift), or other intermediate spacing object, is provided that would tend to divert supporting forces from a fluid in the chamber. Each tubular portion is adapted to have a generally circular cross section when fluid pressure is applied to the chamber. The perimeter of the sheets is selected so that, when fluid pressure is applied to the chamber, the chamber is long enough and wide enough to support the entire weight-bearing surface of the patient's limb so that the entire load borne by the patient's limb is supported by the chamber.

BRIEF DESCRIPTION OF THE DRAWINGS

The features and advantages of the present invention may be more clearly understood when the detailed description of the preferred embodiment provided below is considered in conjunction with the figures, wherein:

FIG. 1 is a schematic plan view of a limb load monitor chamber in accordance with the present invention;

FIGS. 2A and 2B show two cross sections of the chamber, as indicated in FIG. 1;

FIG. 3 is a partial cut away view of an exercise slipper in accordance with the present invention.

DETAILED DESCRIPTION OF THE PREFERRED EMBODIMENTS

Figure 4:
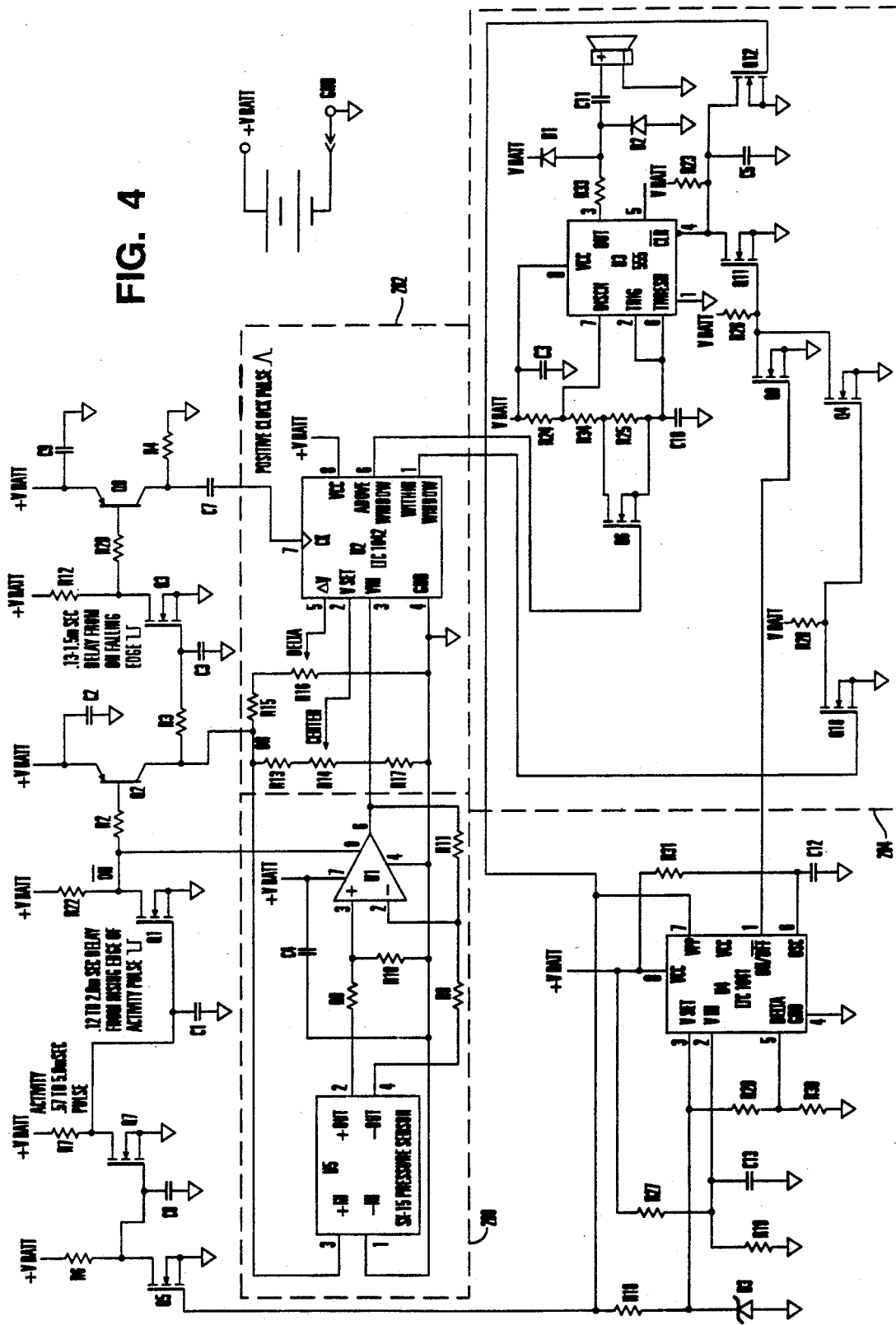
FIG. 4 is a schematic diagram of the sensor circuit.

A plantar chamber 1 in accordance with the present invention is shown in FIG. 1. The chamber is constructed of two parallel sheets of 12 to 15 mil (0.30 to 0.38 mm) polyester urethane film that are sealed together around the perimeter of the chamber by a welded seal 10.

A plurality of longitudinal welds 12 arranged in parallel rows also join the two films inside the chamber defined by the welded seal 10. The rows of longitudinal welds 12 are interrupted along the length of the row so as to provide fluid communication across the length of each row. The interruptions in adjacent rows are alternated so the fluid communication orthogonal to the longitudinal welds 12 in one row is interrupted by an adjacent weld. The welds are formed by RF welding or, alternatively, either by heat welding or one of the other suitable sealing techniques that are well-known in the art.

A urethane tube 14 having an internal diameter of 1/32" (0.8 mm) is inserted through the welded seal 10 in the area of the chamber corresponding to the instep of the patient's foot. The tube is secured by an anchor weld 16 that seals the chamber around the tube 14. Galden D100 or Fluorinert—a perflurinated fluid, is introduced through the tube 14 at a pressure of 80 mm Hg to provide a static base pressure for the monitor's pressure sensor and assure that the patient's weight is supported by the fluid in the chamber 1 at all times. It has been found that perfluorinated fluids provide the following advantages, as compared with other fluids that may have been used for this purpose:

(1) Polar fluids such as water and alcohols permeate the urethane film and the sensor pad thereby loses its base pressure over time, thereby causing variations in the sensitivity of the sensor.

(2) Perfluorinated fluids that have low viscosity, in accordance with the invention do not constitute a slipping hazard, so that, if they leak from the chamber, there is no danger in injury due to slipping accidents. In addition, these materials are not toxic. On the contrary, oils that have been suggested for use in the past don't evaporate, and if they leak they can leave a slippery film on a floor or the like external of the chamber.

(3) The use of gases in the chamber is undesirable since gases vary in volume with changing atmospheric pressure, resulting in variation of the base pressure in the sensor pad and causing variations in the sensitivity of the sensor.

When the fluid is introduced through the tube 14, the portions of the parallel sheets 20, 22 located between the welds 10, 12 are forced into a tubular shape having a substantially circular cross section, as shown in FIGS. 2A and 2B. The longitudinal tubes 24 formed by parallel rows on the longitudinal welds 12 are in fluid communication with adjacent longitudinal tubes through tubular ports 26 formed by the unwelded portions 28 of the films 20, 22 between the ends of the longitudinal welds 12 in each row of welds. However, the unwelded portions 28 in adjacent rows of longitudinal welds 12 are offset, so that there is no direct fluid communication across the width of the plantar chamber 1 perpendicular to the longitudinal welds 12.

FIG. 3 shows a high-top exercise slipper made of durable fabric upper 102 made of 12 to 14 oz. (340 g. to 399 g.) woven nylon, lycra and wool blend 2-way stretch fabric. The center front portion 103 of the slipper 100 lined with a taslan, 3 oz. (85 g.) nylon taffeta, fabric to prevent skin abrasion. The wool upper 102 is stitched to a nylon-backed ⅛" (3.18 mm) thick anti-slip neoprene foam sole 104. Lacing loops 105 are provided on either side of the toe of the slipper 100, so that the toe can be tied to the cuff of the slipper to prevent foot drag. The slipper 100 is held closed by two hook-and-loop fasteners 106 having the hook material sewn to the exterior of the outer side of the slipper 100.

A waterproof urethane-coated taslan sleeve 108 is sewn to the interior of the cuff of the slipper, around the back of the patient's foot above the ankle bone 124. An electronics unit 107, part of which is shown in FIG. 3 is inserted into the sleeve 108 The electronics assembly 107 is made up of two circuit boards. The first circuit board is located at the outer end of the sleeve, and supports two 250 milliamp-hour lithium "coin" batteries, Panasonic Part No. BR2330. The first circuit is connected by a light-weight, twin-lead cable 109 around the back of the patient's foot to a second circuit board that is located at the inner end of the sleeve 108. Both circuits and the cable are closed in a layer of ⅛" (3.18 mm) polyethylene foam padding. Each end of the sleeve 108 is closed by strap 110, which is attached to the sleeve 108 by a hook-and-loop fastener so that the electronics unit 107 is securely held in the sleeve 108 by the straps 110 while the patient is exercising. However, the electronics unit can be easily inserted and removed to replace the batteries or adjust the monitor's load limit. Also, a Molex ™ a pin-and-sleeve connector, which provides a quick disconnect of the negative pole of the batteries on the first circuit board, is thereby made readily accessible to the patient by opening three adjacent hook-and-loop closures on the cuff of the slipper 100.

The plantar chamber 1 in the slipper 100 is covered by a flap 114, made of taslan material that is sewn ;to the bottom edge of the upper 102. An access opening 118 under he instep 116 of the patient's foot is left unsewn to permit installation of the chamber 1 under the flap 114. Plantar chamber 1 and fabric flap 114 cooperate to provide a foot cushion that prevents decubitus ulcers from forming on the patient's foot.

FIG. 4 shows the components of the electronics assembly 107 that appears in phantom inside the sleeve 108 in FIG. 3. The electronics assembly 107 comprises a sensor; circuit 200, a comparator circuit 202 and an alarm circuit 204' The circuits in the electronics assembly 107 of the limb-load monitor are driven by two 3-volt coin-size lithium batteries, and provide reliable monitoring for a period of 90 to 120 days of continuous use before requiring battery replacement.

The tube 14 shown in FIGS. 1 through e is connected to the pressure sensor U5 in the electronics assembly 107. The pressure sensor U5 is a silicon diaphragm, having an integral bridge on one surface of the diaphragm, and is manufactured by Sensym, Inc. of 1255 Reamwood Avenue, Sunnyvale, Calif. 94089, as Part No. SX-15D. The signal output by the pressure sensor is supplied to a programmable operational amplifier U1, which is manufactured by Linear Technology Corp. of 1630 McCarthy Blvd., Milpitas, Calif. 95035, under the Part No. LTC1042. This programmable amplifier U1 is operated in its high-speed, high-power-consumption mode to maximize the gain-bandwidth product and common noise rejection provided for the pressure sensor signal. It has been found that reprogramming amplifier U1 to operate in its high-speed mode each time the monitor circuit is pulsed by Vpp permits the sensor U5, which is rated to operate at 12 to 18VDC to operate reliably at much lower supply voltages. This extension of the sensor's useful operating range unexpectedly provides a net increase in the useful life of the batteries in this unit, even though the total power consumption by U1 is thereby increased.

The comparator circuit 202 uses a monolithic CMOS window comparator manufactured by Linear Technology Corp. under the Part No. LTC1042. The comparator has high-impedance inputs that reduce power consumption during its operation and draws power only during the 80 microsecond active period that is required to latch the output of each comparison. The audio oscillator U3 is a timer manufactured by Maxim Integrated Products, Inc. of 510 N. Astoria Avenue, Sunnyvale, Calif. 94086 under the Part No. ICM7555. This device minimizes current spikes during the oscillator's output transitions to reduce its power consumption, and operates reliably over a wide supply voltage range.

The output of oscillator U3 is supplied to a suitable miniature pienzo audio transducer, such as the miniature piezo ceramic audio element, Part No. SEC 2437, produced by Star Micronics America, Inc. 70-D Ethel Road West, Piscataway, N.J. 08854. The oscillator U3 is protected from the feedback produced by mechanical vibration in the piezo transducer by diodes D1 and D2. The frequency produced by the oscillator U3 is controlled by a CMOS switch Q6 so that a high-pitched 2.1 kHz beep signal is produced when the load limit on the patient's limb is exceeded. A lower-pitched 1.9 kHz beep signal is produced when the comparator U2 detects insufficient pressure in the plantar chamber, or the controller U4 detects a power supply failure.

The controller U4, manufactured by Linear Technology Corp. as Part No. LTC1041, is a bang-bang controller used as a battery monitor. This controller U4 samples the battery voltage at a rate set by resistor R31 at about 2.5 to 3.5 cycles per second. It then compares the battery voltage to a pre-determined minimum valve. The controller's minimum is of 5.6VDC when power is first applied, and is reduced during the operation of the monitor by hysteresis to an effective threshold of 5.2VDC. The result of each such comparison is latched, after approximately 80 microseconds, on pin 1 of U8. During that 80 microsecond interval a positive, switched power output pulse (Vpp) is provided on pin 7 of U4. This power output pulse provides the system strobe for the rest of the electronics assembly 107.

When the pulse (Vpp) provided by pin 7 of U4 goes high at the beginning of the 80 microsecond sampling cycle, Vpp causes the ACTIVITY signal on the drain of Q7 to rise, rendering Q1 conductive after a delay interval of 0.12 to 2.0 msec that is determined by capacitor C1 and resistor R7. After the 80 microsecond sampling cycle is complete, Vpp goes low, which allows capacitor C8 to charge at a rate set by resistor 6, thereby causing Q7 to turn on and ending the ACTIVITY signal. The electronics assembly then enters a low power standby mode.

While the ACTIVITY signal is low, amplifier U1 is programmed for a low-power, mode of operation and transistor Q2, which supplies power to the sensor U5 and reference potentiometers R14 and R16, is in a nonconducting state. The ratiometric comparator U2 does not draw power until its cycle is initiated by a clock pulse that appears on pin 7 of U2, in the response to Vpp. The operation of oscillator U3 is also controlled by the Vpp, which resets the clear input ($\overline{CLR}$) on pin 4 of U3 oscillator when Vpp goes low, after a delay determined by capacitor C5 and resistor R23. This produces an audio signal having approximately a 50% duty cycle.

In the sequence of operation, when Vpp on pin 7 of U4 goes high, amplifier U1 is reprogrammed to operate in the high-speed mode and power is supplied to the sensor U5 and the reference potentiometers R14, R16, as explained above. A clock pulse is then provided to pin 7 of U2, after a settling delay provided by capacitor C3 which allows the output on pin 6 of amplifier U1 to stabilize. After 80 microseconds, the result of the comparison initiated by the clock pulse applied to pin 7 of U2, is latched on pins 1 and 6 of U2. The comparator then turns off its power input, thereby minimizing its power consumption. When the sampling cycle of U4 times out, causing VPP to go low, amplifier U1 is reprogrammed to a low-power operating mode and bipolar transistor Q2 turns off power to the sensor U5 and the reference potentiometers R14, R16.

If the pressure in the plantar chamber 1 falls below the predetermined pressure range set by reference potentiometers R14, R16, pins 1 and 6 on U2 will be latched low, which will cause the oscillator U3 to produce a low-pitched beep tone that is controlled by Vpp as described above. The effect of exceeding the load limit is the same as falling below the pre-determined pressure range, except that pin 6 is then latched high. This high logic state on pin 6 then causes the oscillator U3 to produce the higher-pitched beep tone. Similarly, when U4 detects an insufficient battery voltage, pin 1 of U4 is latched low, which will cause oscillator U3 to produce the low-pitched beep tone, unless the load limit has been exceeded. Again, if the load limit has been exceeded, pin 6 of U2 will be at the high logic state and the higher-pitch tone will be produced by the monitor circuit.

Thus, the electronics assembly 107 uses miniature batteries so that the assembly 107 is small enough and light weight enough to be carried in the sleeve 108 on the cuff of the slipper 100. The monitor circuit in this electronics assembly extends the effective lift of these miniature batteries by using the sampling oscillator internal to U4 to provide the system strobe pulse. This conserves battery power by eliminating the need for a discrete timing oscillator in the circuit.

The active elements of the circuit are also all low-power CMOS devices, with the exception of bipolar transistors Q2 and Q8, and the control circuits internal to U2 and U4 turn off power to the comparators in those devices once the result of each comparison has been latched at the respective output pins, to reduce power consumption. Furthermore, by reprogramming U1 to its high-speed mode each time a pressure comparison is made, this miniature electronics assembly further extends the useful life of its batteries, even though power consumption is thereby temporarily increased.

The extended battery life thus provided makes this limb load monitor device suitable for out-patient use.

Although the invention has been described with particular reference to presently preferred embodiments, it will be apparent to one skilled in the art that other variations and modifications can be made within the spirit and scope of this invention. The invention, however, is defined by the claims appended below. Accordingly it is to be understood that the drawing and the description provided herein are proffered by way of example, to facilitate comprehension of the invention, and should not be construed to limit the scope thereof.

What is claimed is:

1. A pressure transmitting device for a limb load monitor having a pressure sensing device, said transmitting device comprising:
   a flexible fluid chamber having first and second opposed walls, comprising flexible sheets, said device being configured such that said chamber may be positioned in a load-bearing relationship to the entire load-bearing surface of a patient's limb, said chamber having a size and being without internal elements tending to hold said first and second walls apart, whereby said chamber is adapted to support the entire load borne by the patient's limb when fluid pressure is applied to said chamber; and
   means for providing fluid communication between said chamber and the pressure sensing device;
   said fluid chamber including:
   a seal between said sheets forming said chamber between said sheets without any internal spacing or other load supporting elements; and
   further comprising a plurality of second seals between said sheets within said chamber, said second seals being arranged to form tubular portions having a generally circular cross section between said seals when fluid pressure is applied to said chamber through said communication means.

2. The device of claim 1 wherein said seal is an RF-welded seal.

3. The device of claim 1 wherein said seal is a heat-welded seal.

4. The device of claim 1, wherein said second seals are arranged in rows extending longitudinally along said chamber, said rows being interrupted along the length of said rows so that fluid communication is provided across the length of said rows.

5. The device of claim 4 wherein each of said second seals in said chamber extends longitudinally along said chamber and said rows of second seals are interrupted alternately along the length of said rows, so that fluid communication is provided across the length of said rows and fluid communication in a direction orthogonal to one of said second seals is interrupted by an adjacent seal.

6. The device of claim 1 wherein said second seals are RF-welded seals.

7. The device of claim 1 wherein said second seals are heat-welded seals.

8. The pressure transmitting device of claim 1 comprising a fluid in said chamber, said fluid being a perfluorinated liquid.

9. The pressure transmitting device of claim 1 comprising a fluid in said chamber, said fluid being a perfluorinated liquid.

10. A limb load monitor comprising:
    a pressure transmitting device; and
    a pressure sensing device responsive to pressure changes transmitted by said pressure transmitting device,
    said pressure transmitting device including a flexible fluid chamber adapted to be positioned in a load-bearing relationship to the entire load-bearing surface of the patient's limb, said chamber having a size and being without internal spacers, whereby the chamber supports the entire load borne by the patient's limb when fluid pressure is applied to said chamber, and means for providing fluid communication between said chamber and said pressure sensing device.

11. The limb load monitor of claim 10 wherein said pressure sensing device includes means for detecting when a predetermined pressure limit has been exceeded and means for indicating when said predetermined pressure limit has been exceeded.

12. The limb load monitor of claim 11 wherein said pressure sensing device further includes a power source.

13. The limb load monitor of claim 10, wherein said fluid chamber includes:
    first and second flexible sheets; and
    a first seal between said sheets effective to form a chamber between said sheets.

14. The limb load monitor of claim 13, further comprising a plurality of second seals between said sheets within said chamber, said second seals being adapted to form tubular portions having a generally circular cross section between said first and second seals when fluid pressure is applied to said chamber through said communication means.

15. The limb load monitor of claim 14, wherein said second seals are arranged in rows extending longitudinally along said chamber, said rows being interrupted along the length of said rows so that fluid communication is provided across the length of said rows.

16. The limb load monitor of claim 15 wherein each of said second seals in said chamber extends longitudinally along said chamber and said rows of second seals are interrupted alternately along the length of said rows, so that communication is provided across the length of said rows and fluid communication in a direction orthogonal to one second seal is interrupted by an adjacent second seal.

17. A pressure transmitting device for a limb load monitor having a pressure sensing device, said pressure transmitting device comprising:
    a flexible fluid chamber having first and second opposed walls and an exposed surface on one of said walls, said device being configured such that said chamber may be positioned in a load-bearing relationship to an entire load-bearing surface of the patient's limb, said chamber having a size to support the load borne by a patient's limb when fluid pressure is applied to said chamber, said chamber being without internal elements tending to hold said first and second walls apart;
    a perfluorinated liquid in said chamber, and
    means for providing fluid communication between said chamber and the pressure sensing device;
    said walls being flexible sheets of polyurethane elastomer, with a first seal between said sheets forming said chamber therebetween; and
    a plurality of second seals between said sheets within said chamber, said second seals being arranged to form tubular portions having a generally circular cross section between said seals when fluid pressure is applied to said chamber through said communication means.

18. The pressure transmitting device of claim 17 wherein said chamber is fabricated of a polyurethane elastomer.

* * * * *